United States Patent [19]

Banks et al.

[11] Patent Number: 5,468,765

[45] Date of Patent: Nov. 21, 1995

[54] BENZIMIDAZOLE ANTHELMINTIC AGENTS

[75] Inventors: Bernard J. Banks; Christopher J. Dutton, both of Sandwich, United Kingdom; Alexander C. Goudie, Groton, Conn.

[73] Assignee: Pfizer Inc., New York, N.Y.

[21] Appl. No.: 302,707

[22] PCT Filed: Feb. 23, 1993

[86] PCT No.: PCT/EP93/00422

§ 371 Date: Dec. 23, 1994

§ 102(e) Date: Dec. 23, 1994

[87] PCT Pub. No.: WO93/18010

PCT Pub. Date: Sep. 16, 1993

[30] Foreign Application Priority Data

Mar. 12, 1992 [GB] United Kingdom ............... 9205368

[51] Int. Cl.⁶ .................. A61K 31/415; C07D 235/32; C07D 401/04; C07D 405/04
[52] U.S. Cl. .................. 514/395; 546/144; 548/159; 548/194; 548/204; 548/241; 548/304.7; 548/305.1; 548/306.1; 548/308.7; 548/309.4; 514/307; 514/368; 514/370; 514/373; 514/379
[58] Field of Search .............. 546/144; 548/159, 548/194, 204, 241, 304.7, 305.1, 306.1, 308.7, 309.4; 514/307, 368, 370, 373, 379, 395

[56] References Cited

U.S. PATENT DOCUMENTS

| | | | |
|---|---|---|---|
| 3,915,986 | 10/1975 | Gyurik et al. | 260/309.2 |
| 4,002,640 | 1/1977 | Beard et al. | 260/309.2 |
| 4,435,418 | 3/1984 | Chow | 548/306 |
| 4,512,998 | 4/1985 | Nafissi-Varchei | 514/367 |
| 4,826,841 | 5/1989 | Gajewski | 514/237.5 |
| 4,826,862 | 5/1989 | Raeymaekers et al. | 514/388 |

FOREIGN PATENT DOCUMENTS

| | | | |
|---|---|---|---|
| 0328203 | 8/1989 | European Pat. Off. | 548/306.1 |
| 0387941 | 9/1990 | European Pat. Off. | 548/306.1 |
| 1397886 | 6/1975 | United Kingdom | 548/306.1 |
| 1547188 | 6/1979 | United Kingdom | 548/306.1 |
| 9302059 | 2/1993 | WIPO | 548/309.4 |
| 9302058 | 2/1993 | WIPO | 548/309.4 |

Primary Examiner—C. Warren Ivy
Assistant Examiner—Zinna N. Davis
Attorney, Agent, or Firm—Peter C. Richardson; Gregg C. Benson; James T. Jones

[57] ABSTRACT

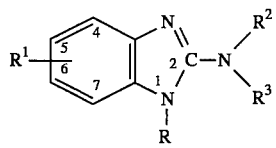

Benzimidazole anthelmintic agents of formula (I) and their non-toxic salts in which R is H, $CO_2(C_1-C_{10}$ alkyl), $-CO_2$(cholester-3-yl) or $-CO_2(CH_2)COOH$ or $-CO_2(CH_2)_nCO_2(C_1-C_6$ alkyl), n=1 to 10, $R^1$ is optionally substituted benzoyl, phenyloxy, phenylthio, phenylsulfonyl, phenylsulfinyl, phenylsulfonyloxy, alkylthio, alkylsulfinyl, alkylsulfonyl, cycloalkylcarbonyl or is selected from a variety of heterocyclic groups and $R^2$ and $R^3$ are independently $-CO_2(C_1-C_4$ alkyl).

13 Claims, No Drawings

BENZIMIDAZOLE ANTHELMINTIC AGENTS

This application is a 371 application of PCT/EP93/00422 filed Feb. 23, 1993.

The present invention relates to certain benzimidazole anthelmintic agents which, quite unexpectedly, are topically and parenterally active and are thus suitable for transdermal and parenteral (especially intramuscular) administration.

These benzimidazole derivatives are represented by the formula:

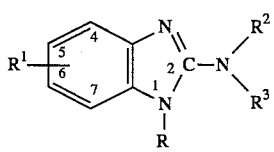

and their non-toxic salts, in which R is H, $-CO_2(C_1-C_{10}$ alkyl), $-CO_2$(cholester-3-yl) or a group of the formula
$-CO_2(CH_2)_n$COOH or $-CO_2(CH_2)_nCO_2(C_1-C_6$alkyl) in which n is an integer of from 1 to 10;

$R^1$ is either (i) benzoyl, phenyloxy, phenylthio, phenylsulfinyl, phenylsulfonyl, phenylsulfonyloxy, $C_1-C_6$ alkylthio, $C_1-C_6$ alkylsulfinyl, $C_1-C_6$ alkylsulfonyl or $(C_3-C_7$ cycloalkyl)carbonyl, said phenyl groups, and the phenyl portion of said benzoyl group, optionally having 1 to 3 substituents each independently selected from halo, $C_1-C_4$ alkyl, halo($C_1-C_4$ alkyl), $C_1-C_4$ alkoxy, $C_1-C_4$ alkylthio, $C_1-C_4$ alkylsulfinyl, $C_1-C_4$ alkylsulfonyl, $C_2-C_4$ alkanoyl, nitro, isothiocyanato, and cyano; or (ii) a group of the formula:

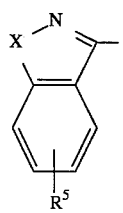

where X is O,S,SO,SO$_2$ or NR$^4$ in which R$_4$ is hydrogen; $C_1-C_4$ alkyl, phenyl or phenyl($C_1-C_4$ alkyl), said phenyl groups being optionally substituted by 1 or 2 substituents each independently selected from $C_1-C_4$ alkyl, halo, hydroxy and $C_1-C_4$ alkoxy; and $R_5$ is H, $C_1-C_4$ alkyl, halo, hydroxy or $C_1-C_4$ alkoxy;

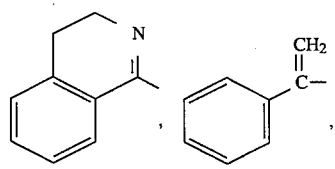

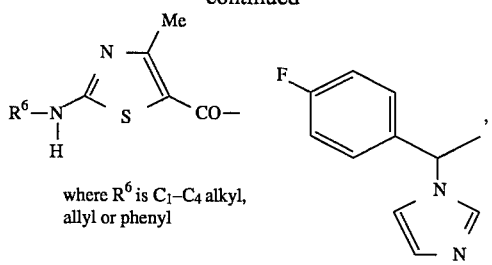

where $R^6$ is $C_1-C_4$ alkyl, allyl or phenyl

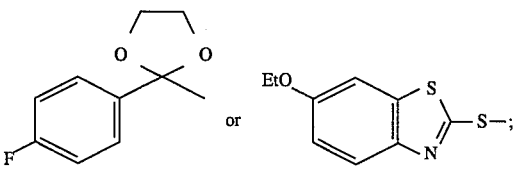

$R^1$ being in the 5(6)-position when R is H, and in the 5-or 6-position when R is other than H;
and $R^2$ and $R^3$ are each independently $-CO_2(C_1-C_4$ alkyl).

Preferred alkyl and alkoxy groups have 1 to 4 carbon atoms.

n is preferably an integer of from 3 to 6.

R is preferably H, $-CO_2(C_1-C_8$ alkyl), $-CO_2$(cholester-3-yl), $-CO_2(CH_2)_n$COOH or $-CO_2(CH_2)_nCO_2-$ $(C_1-C_4$alkyl) where n is an integer of from 3 to 6.

R is most preferably H, $-CO_2(C_1-C_4$ alkyl).

$R^1$ is preferably $C_1-C_4$ alkylthio, $C_1-C_4$ alkylsulphinyl, phenylthio, phenylsulfinyl, benzoyl optionally substituted by halo, phenylsulfonyloxy optionally substituted by halo, or 1,2-benzisoxazol-3-yl.

More preferably, $R^1$ is benzoyl, 4-fluorobenzoyl, 4-fluorophenylsulfonyloxy, n-propylthio, n-propylsulfinyl, phenylthio, phenylsulfinyl, or 1,2-benzisoxazol-3-yl.

Most preferably, $R^1$ is n-propylthio;

$R^2$ and $R^3$ are preferably the same and are both most preferably $-CO_2CH_3$.

Alkyl, alkoxy, alkanoyl, alkenyl and alkynyl groups, when appropriate, can be straight or branched chain. "Halo" means F, Cl, Br or I.

Suitable non-toxic acid addition salts, suitable for veterinary use, are for example the hydrochloride, hydrobromide, and sulphate salts. These can all be prepared conventionally.

The benzimidazoles of the formula (I) and their salts are in particular anthelmintics suitable for the control of parasitic diseases in both human and non-human animals such as sheep, cattle and domestic pets. The compounds exhibit activity against mature and immature parasitic forms of, for example, nematodes, trematodes and cestodes such as are represented by Trichostrongylus, Dictyocaulus, Ostertagia, Nematodirus, Stronglyoides, Trichuris, Haemonchus, Cooperia, Dirofilaria, Toxocara, Trichuris, Fasciola and Monezia species.

Efficient control of these species is achieved by introducing into said animals circulatory system an anthelmintically-effective amount of a compound of the formula (I) or a salt thereof. In the case of these compounds, it has been unexpectedly found that this control can be achieved by percutaneous absorption and/or penetration from a liquid or cream formulation applied directly to the animals' skin. Such liquid formulations are known as "pour-on formulations". Such pour-on formulations are characterised in that the active ingredient, i.e. the compound of the formula (I) or a salt thereof, is dissolved, emulsified or suspended in a suitable solvent or solvent mixture which is tolerable by the skin and non-toxic to the animal, optionally with certain auxiliary ingredients.

To prepare pour-on formulations, the compounds of the formula (I) and their salts are formulated in a conventional manner by mixing them with carriers which are effective in penetrating the skin, the compound (I) then being absorbed by the animal through the skin and transmitted systemically throughout the animal.

The pour on formulation contains:

1. a non volatile drug solvent or solvent mixture which may include solvents normally classed as transdermal penetration enhancers, and, optionally, one or more of the following:

2. a solvent with the specific role of enhancing transdermal penetration if such a solvent is not already present performing function 1 as the main drug solvent;

3. an accessory spreading agent if this auxiliary function is not performed adequately by the drug solvent (1) and any transdermal penetration enhancer (2);

4. a volatile solvent. This volatile solvent may aid the spreading and distribution of components 1 and 2, adjust the formulation to a convenient dosing volume, and ensure solubility and miscibility of the formulation in extreme storage conditions;

and 5. further adjuvants, where necessary; to ensure chemical stability in storage and use, to increase the viscosity of the formulation to prevent run off, to deter other animals from licking the composition off the treated animal, and to protect the skin from undesirable irritation.

Suitable drug solvents (1) are selected to achieve adequate solubility from:

Spreading oils—silicone oils, isopropyl myristate, isopropyl palmitate, caprylic/capric acid triglyceride, saturated triglycerides of naturally occuring fatty acids, fatty acid esters (e.g. ethyl oleate), and fatty acid esters which correspond to synthetic anatine uropygial gland fat.

Aliphatic hydrocarbons—e.g. light paraffin oil.

Hydroxylic solvents—less volatile alcohols (e.g. hexanol, octanol), propylene glycol, polypropylene glycols, ethylene glycol, diethylene glycol, glycerols and ether and or ester substituents of these solvents (e.g. Triacetin), benzyl alcohol and carboxylic acid esters (e.g. benzyl benzoate), butyl acetate, propylene carbonate and ethyl lactate.

Polyalkoxylated solvents—Polyethylene glycols, polyglycol ethers and or esters e.g. 2-(2-alkoxy)ethoxyethanols and 2-(2-alkoxy)ethoxyethyl alkanoates.

Vegetable oils—not included in the definition of spreading oils e.g. corn, sesame, olive, pine, linseed, cottonseed and ground nut oil.

Penetration enhancing agents (2)—
  (a) e.g. dimethylsulphoxide, dimethylformamide and dimethylacetamide;
  (b) Pyrrolidones. In particular 2-pyrrolidone, N-methylpyrrolidone, and 1 or 5 and 1,5 alkyl substituted pyrrolidones e.g. 1,5-dimethyl-2-pyrrolidone or carboxylic acid substituted pyrrolidones;
  (c) alkylsulphoxides, sugar esters and phosphine oxides; and
  (d) azacycloalkan-2-ones.

While these solvents may be used in miscible combinations, miscibility may be achieved by incorporation of a ternary solvent, if required, to provide adequate drug solubility.

Accessory spreading agents (3) comprising spreading oils (if these are not used as the main drug solvent as previously listed in (1)) or surface active agents where the term surface active agent is used to cover materials variously called wetting agents, emulsifying agents and dispersing agents.

These include:

Non-ionic water soluble emulsifiers such as alkylaryl polyglycol ethers, polyoxyethylene alkylaryl ether, alkylpolyglycol ethers, polyoxyethylene esters and ethers, polyoxyethylene sorbitan mono fatty acid esters, sorbitan mono fatty acid esters, ethoxylated nonyl phenols, isooctylphenol, polyethoxyethanol and polyethoxylated castor oil (Cremophor EL$^R$). Anionic surfactants including soaps, fatty sulphate esters (e.g. dodecyl Na sulphate), fatty aromatic sulphonates (e.g. alkylbenzenesulphonates), more complex fatty sulphonates such as the amide condensation product of oleic acid and N-methyltaurine, the sodium sulphonate of dioctylsuccinate and the disodium ethoxylated nonylphenol half ester of sulphosuccinic acid. Cationic agents such as cetyltrimethylammonium bromide may also be used as well as ampholytic surfactants such as di-Na-N-lauryl betaiminodiopropionate or lecithin.

Suitable volatile solvents (4) include:

Ketones such as acetone, methyl ethyl ketone, methyl isobutyl ketone and cyclohexanone; simple alcohols (in particular methanol, ethanol and [especially] isopropylalcohol); straight and branched alkylethers (e.g. dibutyl diisopropyl ether), tetrahydrofuran, glycol ethers and straight and branched chain alkyl acetates (e.g. isopropyl acetate) and other esters such as lactic acid ethyl ester; aromatic hydrocarbons such as xylene, benzene, toluene, alkylnaphthalenes and chlorobenzenes; and aliphatic hydrocarbons such as paraffins of chain length 6–20 and halogenated aliphatic hydrocarbons.

Appropriate auxiliary additives (5) include:

Stability enhancers—antioxidants e.g. ascorbic acid, butylated hydroxyanisole and butylated hydroxytoluene.

Colourants—inorganic pigments, iron (II) oxide, titanium dioxide, Prussian blue; organic dyestuffs e.g. alizarin based, azo dye-based or metal phthalocyanine-based dyestuffs.

Adhesion promoters—carboxymethylcellulose, methylcellulose and other cellulose and starch derivatives, polyacrylates, alginates, gelatines, gum arabic, polyvinylpyrrolidone, copolymers of methylvinyl ether and maleic anhydride, polyethylene glycols, paraffins, oils and waxes, hydrogenated castor oil, lecithins and synthetic phospholipids.

Oral deterrents—such as bitter aloes.

Emolients—such as lanolin.

The drug is dissolved in typical formulations which contain 1–100% of the main drug solvents, usually not more than 70% and ideally not more than 20%. The rest of the formulation is composed in the main by the volatile solvent which may comprise 0–99% of the formulation and preferably not less than 30%. Further transdermal penetration enhancers (0–33%), accessory spreading agents (0–25%) and adjuvants (0–5%) are added as required.

Preferred formulations for the actives were selected from typical formulations.

Examples of some typical formulations are:

| Ingredient | % Composition |
|---|---|
| Formulation 1 | |
| 2-(2-Butoxyethoxy) ethanol | 100 |
| Formulation 2 | |
| 2-(2-Butoxyethoxy) ethanol | 5 |
| Propan-2-ol | 95 |
| Formulation 3 | |
| Ethyl oleate | 50 |
| Isopropyl acetate | 50 |
| Formulation 4 | |
| Dimethylsulphoxide | 20 |
| Xylene | 80 |
| Formulation 5 | |
| Cetyl 2 ethylhexanoate/ stearyl 2-ethylhexanoate blend | 10 |
| Propan-2-ol | 90 |
| Formulation 6 | |
| PEG 300 | 60 |
| iso-octylphenoxypolyethoxyethanol e.g. Triton X-100$^R$ | 10 |
| Propan-2-ol | 30 |
| Formulation 7 | |
| Propylene glycol | 50 |
| Hydroxypropyl cellulose (MW 1 × 10$^6$ Dalton) e.g. Klucel HPC HF$^R$ | 0.5 |
| Butylated hydroxyanisole | 0.02% w/v |
| Ethanol | to 100% |
| Formulation 8 | |
| Propylene glycol | 5 |
| Sodium Erythrosine | 0–0.01% w/v |
| Methanol | to 100% |
| Formulation 9 | |
| Triacetin | 60 |
| Isopropyl acetate | 40 |

The pour-on formulations typically contain the active compound (I) salt thereof in an amount of from 0.5% wt/vol to 60% wt/vol. A typical pour-on formulation would contain 1 to 50 mg of the active ingredient per kg of animal body weight in, say, 0.01–1 ml per kg body weight of the animal. Typically the formulation is simply poured on the animal. Concentrated formulations are often referred to as "spot-on" formulations, which are spotted onto the animal.

The compounds of formula (I) are administered as a formulation appropriate to the specific use envisaged and to the particular species of host animal being treated and the parasite involved. For use as an anthelmintic the compounds may be administered orally in the form of a capsule, bolus, tablet or drench or as a pour-on formulation, or alternatively, they can be administered by injection (e.g. subcutaneously, intramuscularly or intravenously) or as an implant. Such formulations are prepared in a conventional manner in accordance with standard veterinary practice. Thus. capsules, boluses or tablets may be prepared by mixing the active ingredient with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier such that the final formulation contains from 0.5 to 60% by weight of the active ingredient. These formulations will vary with regard to the weight of active compound depending on the species of host animal to be treated, the severity and type of infection and the body weight of the host. For parenteral and oral administration, typical dose ranges of the active ingredient are 1–50 mg per kg of body weight of the animal. Pour-on formulations have been previously described.

As an alternative the compounds may be administered with the animal feedstuff and for this purpose a concentrated feed additive or premix may be prepared for mixing with the normal animal feed.

The compounds of the invention are highly active antiparasitic agents having utility not only as anthelmintics, but as ectoparasiticides, insecticides and antiprotozoal agents.

Thus the compounds are effective in treating a variety of conditions caused by endoparasites including, in particular, helminthiasis which is most frequently caused by a group of parasitic worms described as nematodes, cestodes and trematodes, and which can cause severe economic losses in swine, sheep, horses and cattle as well as affecting domestic animals and poultry. The compounds are also effective against other nematodes which affect various species of animals including, for example, Dirofilaria, Toxocara, Ancyclostoma, Dipylidium, Echinococcus and Taenia in dogs and various parasites which can infect humans including gastrointestinal parasites such as Ancvlostoma, Necator, Ascaris, Strongyloides, Trichinella, Capillaria, Trichuris, Enterobius and parasites which are found in the blood or other tissues and organs such as filarial worms and the extra intestinal stages of Strongyloides and Trichinella.

The compounds are also of value in treating ectoparasite infections including in particular arthropod ectoparasites of animals and birds such as ticks, lice, fleas, blowfly, biting insects and migrating dipterous larvae which can affect cattle and horses.

The compounds are also insecticides active against household pests such as the cockroach, clothes moth, carpet beetle and the housefly.

For use as an insecticide the compounds can be applied as sprays, dusts, emulsions and the like.

The compounds of the formula (I) in which R is H, or in which R and $R^3$ are the same and are $-CO_2(C_1-C_4$ alkyl$)$ can be prepared by alkylating an optionally protected 5(6)-benzimidazole of the formula:

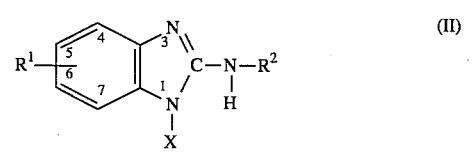

(II)

where $R^1$ is in the 5-(6-) position, $R^1$ and $R^2$ being as defined for formula (I), and X is H or an amino-protecting group, with a compound of the formula:

(III)

where Q is a suitable leaving group, such as chloro, and $R^3$ is as defined for formula (I), followed by removal of the amino-protecting group, if present, to produce a compound (I) in which R is H.

A preferred amino-protecting group is t-butoxycarbonyl.

The reaction is preferably carried out in the presence of an organic or inorganic base such as triethylamine, pyridine or potassium carbonate in an organic solvent at from about 0° to room temperature. Pyridine is a particularly useful solvent as it also acts as a base, but methylene chloride is also useful. The amino-protecting group X, if present, is then removed conventionally to produce compounds in which R is H: for example a t-butoxycarbonyl protecting group is typically removed by reaction with trifluoroacetic acid at from about 0° C. to room temperature.

The compounds of the formula (I) in which R is other than H can also be prepared by the reaction of a compound of the formula (I) in which R is H (prepared as previously described) with a compound of the formula Q—R or R—O—R where Q is a leaving group such as chloro and R is as defined for formula (I) except for H. The reaction is again preferably carried out in the presence of an organic or inorganic base and in a suitable organic solvent, typically at from 0° C. to about room temperature. Pyridine is again the preferred solvent since it can also function as a base. However, methylene chloride is an alternative preferred solvent and in this case triethylamine is the preferred base. The product (I) can then be isolated and purified conventionally.

Because in the benzimidazole end products (I) and starting materials (II) in which R is H, the position of the hydrogen atom at the nitrogen atom of the imidazole ring cannot be determined (tautomerism), it will be appreciated that the compounds are correctly named as 5(6)-substituted benzimidazoles.

Where the products (I) are prepared as mixtures of the 5- and 6- $R^1$-substituted compounds (e.g. as in Example 3), then the 5- and 6- compounds can be separated by conventional techniques such as by fractional recrystallisation and chromatography, particularly reverse-phase hplc.

The starting materials (II) in which X is an amino-protecting group are preparable by the N-protection of the corresponding benzimidazoles having a hydrogen atom at the 1-position with a suitable reagent, e.g. di-t-butyldicarbonate. These "unprotected" benzimidazoles, i.e. the compounds (II) in which X is H, are known compounds and in many cases have generic non-proprietary names, as follows:

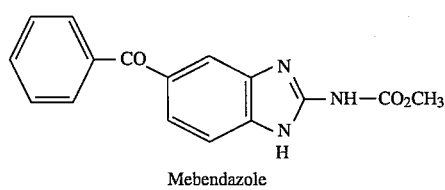

Mebendazole

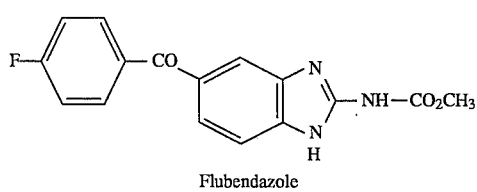

Flubendazole

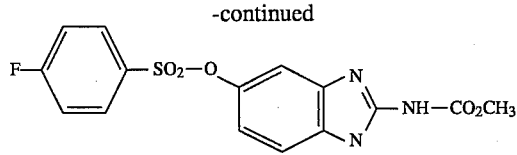

Luxobendazole

Albendazole

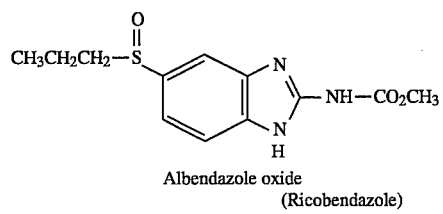

Albendazole oxide
(Ricobendazole)

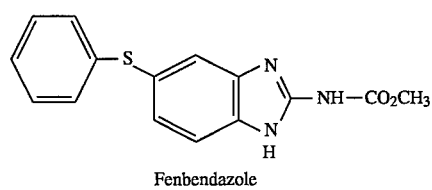

Fenbendazole

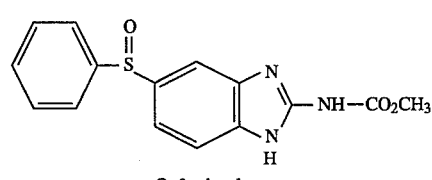

Oxfendazole

For further details of these compounds please also see for example the following references: S. Sharma et.al., Proc. Drug. Res., 1983, 27, 85; O. W. Ostmann et.al., Prog. Antimicrob. Anticancer Chemother, 1969, 1, 159; A. H. M. Raeymaekers, Arzneim-Forsch/Drug. Res., 28(1), 586; E. A. Averkin et.al., J.Med. Chem, 1975, 18, 1164; S. Ram et.al., Org. Prep. Proced. Int, 1985, 17, 215; H. D. Brown et.al., JACS, 1961, 83, 1764; D. R. Hoff et.al., Experientia, 1970, 26, 550; U.S. Pat. No. 3,010,968, GB 1123317; U.S. Pat. Nos. 3,915,986; 4,002,640; 4,435,418; 4,826,841; 4,032,5361; 4,512,998; DE-A-3247615; EP-A-0387941; EP-A-0009174; and ZA-7902975.

$C_1$–$C_6$ Alkylthio groups represented by or present in $R^1$ can be oxidized to $C_1$–$C_6$ alkylsulfinyl or alkylsulfonyl groups by conventional techniques, e.g. by the use of 1 or more equivalents of m-chloroperbenzoic acid, as appropriate, in a suitable solvent such as methylene chloride.

The utility of the compounds as anthelmintics when given transdermally can, for example, be assessed by the following technique:

Male Cobb-Wistar rats weighing 40–50 g (3–4 weeks old) are used. The animals are fed on normal cubed rodent diet containing 60 ppm of the immunosuppressant hydrocortisone acetate. Immunosuppression commences one week prior to infection and is maintained until necropsy. Both food and water are given ad lib.

Each rat is given 1500 *T. colubriformis* infective larvae orally. Ovine-derived larvae are prepared from stock cultures immediately before dosing and checked microscopically for viability. Only motile, viable larvae are used. Parasites are administered in 0.25 ml of water.

One to three weeks post-infection animals are randomly assigned to either treatment (generally 5 rats) or control (generally 10 rats) groups. Solutions of test compounds in appropriate vehicles (see below) are administered topically by pipette to a shaven area (approximately 1 square inch) of the back close to the neck. Drug concentrations in the vehicle are adjusted such that each animal receives the desired dosage in <0.25 ml/100 g body weight. At the time of dosing the weight of the animals ranges from 90 to 110 g. All animals are necropsied three days post-dosing.

At necropsy the small intestine of each animal is removed and placed in a plastic pot containing 20 ml of pepsin digest mixture, comprising pepsin A powder 8 g, NaCl 8.5 g, plus 16 ml concentrated HCl in 1 L of distilled water. The digests are incubated at 37° C. for 4 hours prior to washing over a 75 um sieve with a high pressure water spray. Worms retained on the sieve are collected by washing into fresh pots and stained using an iodine/potassium iodide solution comprising iodine 30 g, potassium iodide 40 g, plus 30 ml methylated spirits in 70 ml distilled water. The contents of each pot is then diluted to a final volume of 500 ml with distilled water and a 50 ml aliquot taken for worm counting. The efficacy of each drug treatment is determined as the percent reduction from the average worm burden of untreated controls.

The following Examples illustrate the preparation of the compounds of the formula (I). The Preparation illustrates the preparation of a starting material.

Preparation 1

Preparation of 2-(methoxycarbonylamino)-1-(t-butoxycarbonyl)-(5- and 6-n-propylthio)benzimidazole To a stirred suspension of methyl 5(6)-n-propylthiobenzimidazole-2-carbamate(albendazole) (150 g, 0.57M) in 2 L of tetrahydrofuran was added 123 g (0.57M) of di-t-butyl dicarbonate. The mixture was stirred for 18 hours at room temperature and then for 5.5 hours at 50° C. A further 62 g of di-t-butyl dicarbonate in 150 ml of tetrahydrofuran was then added. The mixture was stirred for 18 hours at room temperature then for a further 2 hours at 50° C. After evaporation, the residue was slurried with diethyl ether (1 L) and filtered. The filtrate was evaporated and crystallized from n-hexane to yield 66 g of a mixture of the title compounds. The filter cake was slurried with methylene chloride, filtered and the filtrate was evaporated. The residue was crystallized from n-hexane to yield a further 61 g of the title compounds.

Analysis: Found: C,55.91%; H,6.41%; N,11.58%. $C_{17}H_{23}N_3O_4S$ requires: C,55.87%; H,6.34%; N,11.50%. M.Pt. 85°–87° C.

EXAMPLE 1

Preparation of 2[(Bis-methoxycarbonyl)amino]-(5(6)-n-propylthio)benzimidazole

To a stirred solution of 2-(Methoxycarbonylamino)- 1-(t-butoxycarbonyl)-(5- and 6-n-propylthio)-benzimidazole (101.3 g, 0.28M, prepared as in Preparation 1) in 500 ml of pyridine at 0° C. was added 87 ml (1.12M) of methyl chloroformate over 30 minutes.

The mixture was allowed to warm to 20° C. and then stirred for 48 hours. A further 50 ml (0.64M) of methyl chloroformate was added over 30 minutes with cooling. After stirring for 2 hours at 20° C. a further 57 ml (0.73M) of methyl chloroformate was added and the reaction mixture stirred for 18 hours at 20° C. Then a further 50 ml (0.64M) of methyl chloroformate was added along with 50 ml, of pyridine. After stirring for 3 hours at 20° C, the reaction mixture was partitioned between ethyl acetate (500 ml) and water (500 ml). The ethyl acetate layer was dried over sodium sulphate and filtered, then evaporated in vacuo. The residue was treated with trifluoroacetic acid (400 ml) at –10° C., then allowed to warm to 20° C. and stirred for 1 hour. The reaction mixture was evaporated in vacuo and the residue partitioned between ethyl acetate (400 ml) and saturated aqueous sodium bicarbonate solution (400 ml). The ethyl acetate layer was separated and washed with water (400 ml). The aqueous layer was back-extracted with more ethyl acetate (200 ml) and the combined organic layers were dried over sodium sulphate, filtered and evaporated to dryness. The residue was suspended in methylene chloride (200 ml) and filtered. The filtrate was evaporated to dryness. The residue was crystallized from diethyl ether and hexane to yield 60 g of the title compound.

Analysis %: Found: C, 51.65; H, 5.14; N, 12.92; $C_{14}H_{17}N_3O_4S$ requires: C, 52.00; H, 5.30; N, 12.99. M.Pt. 114.5°–117.7°.

EXAMPLE 2

Preparation of 2-[(Bis-methoxycarbonyl)amino]-1-(n-butyloxycarbonl)-(5- and 6-n-propylthio)-benzimidazole To a stirred solution of 2-[(bis-methoxycarbonyl)amino]-5(6)-n-propylthio)benzimidazole (1.0 g, 3.1 mmol, see Example 1) in 5 ml of pyridine at 0° C. was added 0.8 ml (6.2 mmol) of n-butyl chloroformate. The mixture was then allowed to warm to 20° C. and stirred for 4 hours. The mixture was then partitioned between 1N hydrochloric acid (50 ml) and ethyl acetate (50 ml). The ethyl acetate layer was then washed with water and dried over magnesium sulphate. Then the solution was filtered and evaporated to dryness in vacuo. The residue was extracted with hot hexane and the extract crystallized to yield 0.7 g of a mixture of the title compounds.

Analysis %: Found: C, 54.22; H, 6.33; N, 9.75; $C_{19}H_{25}N_3O_6S$ requires: C, 53.90; H, 5.95; N, 9.92. M. Pt. 87.6°–90.5° C.

EXAMPLE 3

Preparation of 2-[(Bis-methoxycarbonyl)amino]-1-(n-octyloxycarbonyl)-(5- and 6-n-propylthio)benzimidazole The procedure of Example 2 was followed but using n-octyl chloroformate (6.6 g, 34 mmol) instead of n-butyl chloroformate and the other reagents pro rata to yield 7 g of a mixture of the title compounds as an oil.

Analysis %: Found: C, 57.71; H, 6.48; N, 8.39; $C_{23}H_{33}N_3O_6S$ requires: C, 57.60; H, 6.94; N, 8.76. M. Pt. 65°–67° C.

EXAMPLE 4

Preparation of 2[(Bis-methoxycarbonyl)amino]-1-(cholester-3-yloxycarbonyl)-(5- and 6-n-propylthio)benzimidazole To a solution of 2-[(bis-methoxycarbonyl)amino]-( 5(6)-n-propylthio)benzimidazole (5 g, 15.5 mmol) in 100 ml of methylene chloride was added 7.6 g (17 mmol) of cholester-3-yl chloroformate and 2.4 ml (17 mmol) of triethylamine. The mixture was then stirred at 20° C. for 2 hours, evaporated in vacuo, and the residue was suspended in diethyl ether and filtered. The filtrate was then passed through a plug of silica (Merck, "silica gel 60", [Trade Mark] 25 g) and washed off with more ether. The filtrate was evaporated in vacuo to yield a mixture of the title compounds, 11 g.

Analysis %: Found: C, 68.99; H, 8.68; N, 5.31; $C_{42}H_{61}N_3O_6S$ requires: C, 68.54; H, 8.35; N, 5.71. M. Pt. 65°–67° C.

EXAMPLE 5

Preparation of 2-[(Bis-methoxycarbonl)amino]-1-(5-[t-butyloxycarbonl]pentyloxycarbonyl)(5- and 6-n-propylthio)benzimidazole and the corresponding 1-(5-carboxypentyloxycarbonyl) compounds To a stirred suspension of t-butyl 6-hydroxyhexanoate (J. Org. Chem., 1980, 45, 3081–3084) (1.0 g, 2.4 mmol), potassium carbonate (0.4 g, 7.8 mmol) in toluene (10 ml) at 0° C. was added, dropwise over 10 minutes, 2.7 ml (3.12 mmol) of a 12.5% solution of phosgene in toluene. The mixture was stirred at 0° C. for 30 minutes then allowed to warm to 20° C. and stirred for 1 hour. The mixture was then purged with nitrogen for 1 hour and evaporated in vacuo. The product was filtered through magnesium sulphate, washed with dry ether and evaporated in vacuo. The residue was added to a solution of 2-[(bis-methoxycarbonyl)amino]-5(6)-n-propylthio)benzimidazole (0.38 g, 1.2 mmol) in pyridine (5 ml) at 0° C. with stirring. The mixture was then allowed to warm to 20° C. and stirred for 18 hours. The mixture was then partitioned between diethyl ether (50 ml) and 1N hydrochloric acid (50 ml). The ether layer was dried over sodium sulphate, filtered and evaporated in vacuo. The product was purified by chromatography on silica (Merck, "silica gel 60" Trade Mark, 25 g,) , eluting with diethyl ether/hexane (80/20) to yield 0.26 g of a mixture of the title compounds as the t-butyl esters.

The free acids were obtained by treatment of the mixture of the esters with trifluoroacetic acid (10 ml) followed by evaporation in vacuo to yield 0.1 g of a mixture of the title acids.

EXAMPLE 6

Preparation of 2-[(Bis-methoxycarbonyl)amino]-1-(methoxycarbonyl)-(5- and 6-n-propylthio)benzimidazole To a slurry of albendazole (25 g, 0.19M) in 200 ml of pyridine was added 50 ml (0.65M) of methyl chloroformate, dropwise, at 0° C. The mixture was allowed to warm to 20° C. and stirred at this temperature for 1 hour, then partitioned between ethyl acetate (200 ml) and 1N hydrochloric acid (200 ml). The ethyl acetate layer was dried over magnesium sulphate, filtered and evaporated. The residue was extracted with hot hexane and the extract crystallized to yield. 11.4 g of a mixture of the title compounds.

Analysis %: Found: C, 50.51; H, 4.51; N, 10.96; $C_{16}H_{19}N_3O_6S$ requires: C, 50.39; H, 4.99; N, 11.02. M. Pt. 83.2°–85.8° C.

EXAMPLE 7

Preparation of 2-[(Bis-methoxycarbonyl)amino]-1-(methoxycarbonyl)-(5- and 6-phenylthio)benzimidazole The procedure of Example 6 was followed but using fenbendazole (5.0 g, 17 mmol) instead of albendazole, and the other reagents pro rata, to yield 4.2 g of a mixture of the title compounds.

Analysis %: Found: C, 54.80; H, 4.10; N, 10.27; $C_{19}H_{17}N_3O_6S$ requires: C 54.93; H, 4.12; N, 10.17. M. Pt. 140.5°–147.2° C.

We claim:

1. A compound of formula (I)

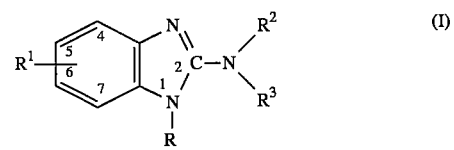

or their non-toxic salt, in which R is H, $-CO_2(C_1-C_{10}$ alkyl), $-CO_2$(cholester-3-yl) or a group of the formula $-CO_2(CH_2)_nCOOH$ or $-CO_2(CH_2)_nCO_2(C_1-C_6 alkyl)$ in which n is an integer of from 1 to 10;

$R^1$ is either (i) benzoyl, phenyloxy, phenylthio, phenylsulfinyl, phenylsulfonyl, phenylsulfonyloxy, $C_1-C_6$ alkylthio, $C_1-C_6$ alkylsulfinyl, $C_1-C_6$ alkylsulfonyl or ($C_3-C_7$ cycloalkyl)carbonyl, said phenyl groups, and the phenyl portion of said benzoyl group, optionally having 1 to 3 substituents each independently selected from halo, $C_1-C_4$ alkyl, halo($C_1-C_4$ alkyl), $C_1-C_4$ alkoxy, $C_1-C_4$ alkylthio, $C_1-C_4$ alkylsulfinyl, $C_1-C_4$ alkylsulfonyl, $C_2-C_4$ alkanoyl, nitro, isothiocyanato, and cyano; or (ii) a group of the formula:

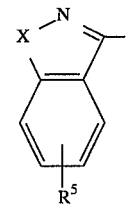

where X is $O, S, SO, SO_2$ or $NR^4$ in which $R^4$ is hydrogen, $C_1-C_4$ alkyl, phenyl or phenyl($C_1-C_4$ alkyl), said phenyl groups being optionally substituted by 1 or 2 substituents each independently selected from $C_1-C_4$ alkyl, halo, hydroxy and $C_1-C_4$ alkoxy; and $R_5$ is H, $C_1-C_4$ alkyl, halo, hydroxy or $C_1-C_4$alkoxy;

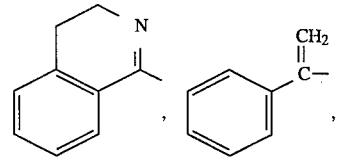

-continued

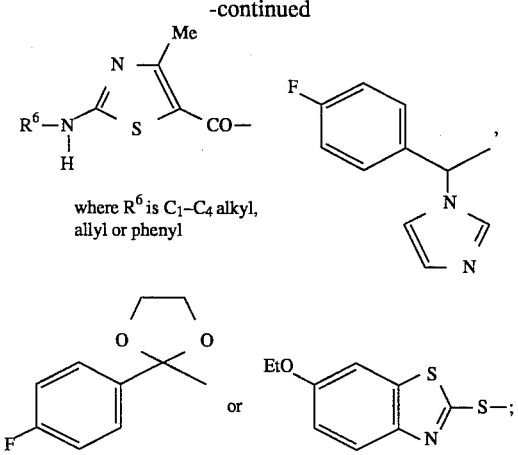

where R⁶ is C₁–C₄ alkyl, allyl or phenyl $R^1$ being in the 5(6)-position when R is H, and in the 5- or 6-position when R is other than H; and $R^2$ and $R^3$ are each independently —CO₂(C₁–C₄ alkyl).

2. A compound according to claim 1, in which n is from 1 to 3.

3. A compound according to claim 1, in which R is H, —CO₂(C₁–C₈ alkyl), —CO₂ (cholester-3-yl), —CO₂(CH₂)ₙCOOH or —CO₂(CH₂)ₙ—CO₂—(C₁–C₄ alkyl).

4. A compound according to claim 3, in which R is H or —CO₂(C₁–C₄ alkyl).

5. A compound according to claim 1, in which said alkyl groups in R have from 1 to 4 carbon atoms.

6. A compound according to claim 1, in which $R^1$ is C₁–C₄ alkylthio, C₁–C₄ alkylsulfinyl, phenylthio, phenylsulfinyl, benzoyl optionally substituted by halo, phenylsulfonyloxy optionally substituted by halo, or 1,2-benzisoxazol-3-yl.

7. A compound according to claim 6, in which $R^1$ is benzoyl, 4-fluorobenzoyl, 4-fluorophenylsulfonyloxy, n-propylthio, n-propylsulfinyl, phenylthio, phenylsulfinyl or 1,2-benzisoxazol-3-yl.

8. A compound according to claim 7, in which $R^1$ is n-propylthio.

9. A compound according to claim 1, in which $R^2$ and $R^3$ are both —CO₂CH₃.

10. An anthelmintic composition comprising a compound as claimed in claim 1 and a pharmaceutically or veterinally-acceptable carrier.

11. An anthelmintic pour-on or spot-on composition for application to the skin of an animal, which comprises a compound according to claim 1 and a veterinally-acceptable carrier effective for passing the compound through the skin of the animal.

12. A method of combating helminths in an animal, which comprises applying to the skin of said animal an amount sufficient to exert an anthelmintic effect of a compound according to claim 1 whereby said compound is absorbed through the skin.

13. A method of combating helminths in an animal, which comprises administering orally or parenterally to said animal an anthelmintically effective amount of a compound according to claim 1.

* * * * *